US009763635B2

(12) United States Patent
Hladuvka et al.

(10) Patent No.: US 9,763,635 B2
(45) Date of Patent: Sep. 19, 2017

(54) METHOD, APPARATUS AND SYSTEM FOR IDENTIFYING A SPECIFIC PART OF A SPINE IN AN IMAGE

(71) Applicants: Agfa Healthcare NV, Mortsel (BE); VRVIS ZENTRUM FUER VIRTUAL REALITY UND VISUALISIERUNG FORSCHUNGS-GMBH, Vienna (AT); IMP FORSCHUNGSINSTITUT FUER MOLEKULARE PATHOLOGIE GMBH, Vienna (AT)

(72) Inventors: Jiri Hladuvka, Mortsel (BE); David Major, Mortsel (BE); Katja Buehler, Mortsel (BE)

(73) Assignees: AGFA HEALTHCARE NV, Mortsel (BE); VRVIS ZENTRUM FÜR VIRTUAL REALITY UND VISUALISIERUNG FORSCHUNGS-GMB, Vienna (AT); IMP FORSCHUNGINSTITUT FÜR MOLEKULARE PATHOLOGIE GMBH, Vienna (AT)

( * ) Notice: Subject to any disclaimer, the term of this patent is extended or adjusted under 35 U.S.C. 154(b) by 0 days.

(21) Appl. No.: 14/761,317

(22) PCT Filed: Jan. 20, 2014

(86) PCT No.: PCT/EP2014/051014
§ 371 (c)(1),
(2) Date: Jul. 16, 2015

(87) PCT Pub. No.: WO2014/114588
PCT Pub. Date: Jul. 31, 2014

(65) Prior Publication Data

US 2015/0356729 A1 Dec. 10, 2015

Related U.S. Application Data

(60) Provisional application No. 61/755,995, filed on Jan. 24, 2013.

(30) Foreign Application Priority Data

Jan. 22, 2013 (EP) .................................... 13152169

(51) Int. Cl.
*G06T 7/00* (2017.01)
*A61B 6/00* (2006.01)
(Continued)

(52) U.S. Cl.
CPC .............. *A61B 6/505* (2013.01); *A61B 5/107* (2013.01); *A61B 5/1075* (2013.01); *A61B 6/032* (2013.01);
(Continued)

(58) Field of Classification Search
CPC ....... A61B 6/032; A61B 6/505; A61B 6/5217; A61B 5/107; A61B 5/1075; A61B 6/468;
(Continued)

(56) References Cited

U.S. PATENT DOCUMENTS 5,570,404 A * 10/1996 Liang .................... A61B 6/504 378/8
2009/0169087 A1 7/2009 Doi et al.
(Continued)

OTHER PUBLICATIONS

Inesta et al. "On the Possibility of Objective Identification of Human Vertebrae Through Pattern Recognition Algorithms." Fifth International Conference on Image Processing and Its Applications, Jul. 4, 1995, pp. 148-152.*
(Continued)

*Primary Examiner* — Jon Chang
(74) *Attorney, Agent, or Firm* — Keating & Bennett, LLP

(57) ABSTRACT

A method, apparatus, and system for reliably identifying a specific part of a spine in an image of a human or animal body, includes the steps of determining one or more parts of the spine in the image, determining one or more discriminative parameters for each of the one or more parts of the
(Continued)

spine in the image, the discriminative parameters relating to at least one anatomical property of each of the one or more parts of the spine, classifying the discriminative parameters of the one or more parts of the spine in the image, and identifying a specific part of the spine based on the classification of the discriminative parameters of the one or more parts of the spine in the image. An identified vertebra, in particular the T12 vertebra and/or its associated intervertebral discs, can be used advantageously as a starting point of powerful automatic spine labeling algorithms.

5 Claims, 2 Drawing Sheets

(51) Int. Cl.

| | |
|---|---|
| ***A61B 6/03*** | (2006.01) |
| ***G06K 9/00*** | (2006.01) |
| ***G06K 9/46*** | (2006.01) |
| ***G06T 5/00*** | (2006.01) |
| ***A61B 5/107*** | (2006.01) |

(52) U.S. Cl.
CPC ........ *A61B 6/5217* (2013.01); *G06K 9/00536* (2013.01); *G06K 9/4609* (2013.01); *G06T 5/002* (2013.01); *G06T 7/0012* (2013.01); *A61B 6/468* (2013.01); *G06K 2209/055* (2013.01); *G06T 2207/10081* (2013.01); *G06T 2207/30012* (2013.01)

(58) Field of Classification Search
CPC .................. G06T 5/002; G06T 7/0012; G06T 2207/30012; G06T 2207/10081; G06K 9/4609; G06K 9/00536; G06K 2209/055
USPC .......................................................... 382/131
See application file for complete search history.

(56) References Cited

U.S. PATENT DOCUMENTS

2009/0245608 A1* 10/2009 Wan ...................... G06T 7/0042 382/131
2011/0130653 A1 6/2011 Wang
2012/0106810 A1 5/2012 Ramakrishnan et al.
2012/0143090 A1 6/2012 Hay et al.
2013/0108135 A1* 5/2013 Huo ...................... G06T 7/0083 382/132

OTHER PUBLICATIONS

Official Communication issued in International Patent Application No. PCT/EP2014/051014, mailed on Mar. 11, 2014.
Ehm et al., "Automated Vertebra Identification in CT Images", Proceedings of SPIE, SPIE—International Society for Optical Engineering, vol. 7259, XP009169525, Mar. 27, 2009, 11 pages.
Ma et al., "Hierarchical Segmentation and Identification of Thoracic Vertebra Using Learning-Based Edge Detection and Coarse-to-Fine Deformable Model", URL:http://www.cs.jhu.edu/~lelu/publication/MICCA-Vertebra-2010.pdf, retrieved on Jun. 19, 2013, XP55067449, 9 pages.
Klinder et al., "Automated model-based vertebra detection, identification, and segmentation in CT images", Medical Image Analysis, Oxford University Press, XP26089345, vol. 13, No. 3, 2009, pp. 471-482.
Oktay et al., "Localization of the Lumbar Discs using Machine Learning and Exact Probabilistic Inference", URL: http://vision.gyte.edu.tr/publications/2011/finalMiccai.pdf, retrieved on Jun. 24, 2013, XP55067900, 8 pages.
Grivas et al., "Segmental Patterns of Rib-Vertebra Angles in Chest Radiographs of Children: Changes Related to Rib Level, Age, Sex, Side and Significance for Scoliosis", Clinical Anatomy, XP8163253, 1992, pp. 272-288.
Gavrielides et al., "Alignment of full and partial CT thoracic scans using bony structures", SPIE, vol. 614461443A-1, XP40220582, 2006, 9 pages.

* cited by examiner

METHOD, APPARATUS AND SYSTEM FOR IDENTIFYING A SPECIFIC PART OF A SPINE IN AN IMAGE

CROSS-REFERENCE TO RELATED APPLICATIONS

This application is a 371 National Stage Application of PCT/EP2014/051014, filed Jan. 20, 2014. This application claims the benefit of U.S. Provisional Application No. 61/755,995, filed Jan. 24, 2013, which is incorporated by reference herein in its entirety. In addition, this application claims the benefit of European Application No. 13152169.2, filed Jan. 22, 2013, which is also incorporated by reference herein in its entirety.

BACKGROUND OF THE INVENTION

1. Field of the Invention

The present invention relates to a method and corresponding apparatus and system for identifying a specific part, in particular a specific vertebra, of a spine in an image, in particular a computed tomography (CT) image, of a human or animal body.

2. Description of the Related Art

The acquisition of CT images with and without contrast agent of abdomen, thorax and/or neck is a routine procedure for the diagnosis of a multitude of diseases or injuries. The spinal column represents a natural reference structure of the upper part of the body for describing the locations of organs and pathologies. To be used as a reference system in daily clinical routine, the vertebrae and/or intervertebral disks in the image have to be labeled. A manual labeling can be time consuming, especially if only arbitrary parts of the spine are visible in the data. Therefore, automatic approaches which deliver labeling results after image acquisition without any user interaction are of interest.

When automatically labeling thorax/lumbar portions of a spine in CT scans it is necessary to assign a correct anatomic intervertebral disc label to a starting point. For example, being the bottommost vertebra with ribs, the T12 vertebra and its associated intervertebral discs are natural candidates for starting points of a spine labeling algorithm. It turned out, however, that a reliable discrimination of the T12 vertebra from other vertebrae in a lumbar-thoracic CT scan is not trivial and can even become hard especially in partial scans, i.e., when image data showing only some of lumbar and/or some of thoracic vertebrae. The ribs attached to the T12 vertebra vary in length and form and may exhibit anatomical similarity with the transversal processes of the L1 vertebra. This may confuse even domain experts and will generally bias any unaware attempts on automated initialization of the labeling algorithm from T12.

SUMMARY OF THE INVENTION

Preferred embodiments of the invention provide a method, apparatus and system for a reliable identification of a specific part, in particular a specific vertebra, of a spine in an image of a human or animal body.

The preferred embodiments are achieved by the method, apparatus and system described below.

A method according to a preferred embodiment of the invention comprises the following steps: determining one or more parts, in particular vertebrae, of the spine in the image; determining one or more discriminative parameters for each of said parts of the spine in the image, wherein the discriminative parameters relate to at least one anatomical property of each of said parts of the spine; classifying the discriminative parameters of said parts of the spine in the image; and identifying said specific part of the spine based on the classification of the discriminative parameters of said parts of the spine in the image.

The apparatus according to a preferred embodiment of the invention comprises an image processing unit for executing the following steps: determining one or more parts, in particular vertebrae, of the spine in the image; determining one or more discriminative parameters for each of said parts of the spine in the image, wherein the discriminative parameters relate to at least one anatomical property of each of said parts of the spine; classifying the discriminative parameters of said parts of the spine in the image; and identifying said specific part of the spine based on the classification of the discriminative parameters of said parts of the spine in the image.

The system according to a preferred embodiment of the invention comprises an image acquisition unit, in particular a computed tomography (CT) unit, for acquiring at least one image of at least a part of a human or animal body and an apparatus according to a preferred embodiment of the invention for identifying a specific part of a spine, in particular a specific vertebra, in the image.

Preferred embodiments of the invention are based on the approach to automatically identify a specific vertebra, preferably the T12 vertebra, in an image of a spine or a part thereof. To this end, one or more discriminative parameters for each of at least two vertebrae contained in the image of the spine are determined, wherein the discriminative parameters relate to the shape of each of the vertebrae. For example, the discriminative parameters characterize the length and/or angle of transverse processes and/or ribs attached to each of the vertebrae. The discriminative parameters determined for each of the vertebrae are classified into two or more different classes. For example, the discriminative parameters are separated, i.e. classified, into three different classes of vertebrae of the lumbar region (L vertebrae), the thoracic region (T vertebrae) and lumbar-thoracic transition region (comprising, e.g., the T12 vertebra) of the spine. Based on the discriminative parameters that were classified into a class corresponding to vertebrae of a specific region of the spine, e.g. the lumbar-thoracic transition region, a respective vertebra is identified as the specific vertebra, e.g. the T12 vertebra.

By preferred embodiments of the invention, a specific part, in particular a specific vertebra, of a spine in an image of a human or animal body can be identified reliably and easily.

According to a preferred embodiment of the invention, the image of the spine contains image information about at least one, preferably at least two, lumbar vertebra and at least one, preferably at least two, thoracic vertebra. By this, the T12 vertebra can be discriminated in a particular reliable way.

Moreover, it is preferred that the discriminative parameters relate to transverse processes at, preferably each of, said parts, in particular vertebra, of the spine in the image. The transverse processes of a vertebra, two in number, serve for the attachment of muscles and ligaments and project one at either side from the point of a vertebra where the lamina joins the pedicle, between the superior and inferior articular processes. Discriminative parameters relating to transverse processes of the vertebrae turned out to be highly conclusive characteristic values for discriminating specific vertebrae. Thus, the reliability of the identification of specific vertebra is further enhanced.

Alternatively or additionally, the discriminative parameters relate to ribs at, preferably each of, said parts, in particular vertebra, of the spine in the image. Likewise, discriminative parameters relating to a rib or the ribs attached to a vertebra are highly conclusive characteristic values for discriminating specific vertebrae. By this, the reliability of the identification of specific vertebra is also enhanced.

In a further preferred embodiment of the invention, the discriminative parameters relate to a length of the transverse processes or ribs, respectively, at said parts of the spine in the image. Preferably, the length of a transverse or rib corresponds to a distance between a centroid of a vertebra and a tip of a transverse process or rib, respectively, associated with the vertebra. Preferably, the coordinates of the tip of the associated transverse process or rib, respectively, correspond to the coordinates of a local maximum in the image of the spine. One or more of these embodiments contribute to a particular reliable identification of a specific vertebra in the image.

In another preferred embodiment of the invention, the discriminative parameters relate to an angle of the transverse processes or ribs, respectively, at said parts of the spine in the image. Preferably, the angle of the transverse processes or ribs, respectively, corresponds to an angle between two straight lines connecting a centroid of a vertebra with the tips of two transverse processes or ribs, respectively, associated with the vertebra. Likewise, by these embodiments the identification of a specific vertebra in the image becomes particularly reliable.

It is particularly preferred that the discriminative parameters of a part of the spine, in particular of a vertebra, comprise both the length and the angle of the transverse processes or ribs, respectively, associated with the vertebra. It was surprisingly found that an evaluation of these two parameters for each of the vertebrae allows for a particularly reliable discrimination of specific vertebrae in the image, in particular the T12 vertebra.

According to a further preferred embodiment of the invention, the discriminative parameters of said parts of the spine in the image are classified by a support vector machine (SVM). A SVM according to a preferred embodiment of the invention is a learning model with an associated learning algorithm which analyzes input data for performing a classification by assigning a set of input data, i.e. a set of discriminative parameters of a vertebra, into one category or class out of a given number of categories or classes, respectively. By an SVM, a particularly reliable discrimination of specific vertebrae, in particular of the T12 vertebra, can be achieved.

Preferably, said parts, in particular vertebrae, of the spine in the image of the body are determined on the basis of a contour image which is derived from the image of the body by at least one of the following steps: detecting the spinal canal of the spine in the, preferably three-dimensional, image of the body; pruning away a frontal part of a rib cage from the image of the body; calculating a, preferably two-dimensional, maximum intensity projection (MIP) of the image of the body; deriving a binary image from the maximum intensity projection (MIP) of the image of the body by comparing pixel values of the maximum intensity projection (MIP) with at least one bone threshold value; deriving the contour image from the binary image. By determining the discriminative parameters from image data of a two-dimensional contour image, which is obtained by at least one of the afore-mentioned steps, a specific vertebra can be identified with particularly high precision.

Preferably, said parts, in particular vertebrae, of the spine in the image of the body are determined on the basis of the contour image by at least one of the following steps: smoothing the contour image; calculating local minima and local maxima in the contour image; determining vertebra centers, in particular centroids, on the basis of said local minima and/or local maxima; establishing connections between said vertebra centers with corresponding local maxima; determining said discriminative parameters for said parts of the spine in the image on the basis of said connections, in particular determining the lengths and/or angles of said connections. By a determination of the discriminative parameters according to at least one of the afore-mentioned steps, a specific vertebra, in particular the T12 vertebra, can be identified with extraordinary precision and reliability.

As stated in the introductory part, powerful algorithms for automatic labeling of thorax and/or lumbar portions of a spine require an assignment of a correct anatomic intervertebral disc label, e.g. the T12 vertebra and its associated intervertebral discs, as a starting point. Accordingly, a particularly preferred and advantageous application of preferred embodiments of the invention relates to a method for labeling one or more parts of a spine in an image, in particular a computed tomography (CT) image, of a human or animal body, comprising the following steps: i) matching a model of a spine segment with segments of the spine in the image by starting matching said model of a spine segment with an initial segment of the spine in the image, wherein said initial segment of the spine in the image comprising an initial part of the spine in the image, and continuing matching said model of a spine segment with one or more further segments of the spine in the image, wherein said further segments of the spine in the image comprising further parts of the spine in the image, and ii) labeling one or more parts of the spine in the image dependent on the result of the matching according to step i), wherein the initial part of the spine in the image corresponds to the specific part of the spine in the image which is identified by the method according to a preferred embodiment of the invention. Since an identification of a specific part of the spine, in particular the T12 vertebra, is achieved with high preciseness and reliability, the subsequent labeling of the remaining vertebrae and/or intervertebral discs in the image starting at the initial/specific vertebra, which was determined according to preferred embodiments of the invention, is accordingly reliable.

In the context of the invention, the term “part of a spine” preferably relates to a vertebra or intervertebral disk of a spine. The terms “spine segment” and “segment of a spine” preferably relate to a portion of a spine comprising one or more parts of the spine, in particular one or more vertebrae and/or intervertebral disks. Accordingly, an “initial segment of the spine” or a “further segment of the spine” comprises one or more parts of the spine located at an initial or a further position, respectively, on or along the spine. Further, the term “matching” relates to a comparison of said model of a spine segment with segments of the spine in the image and/or an examination whether the model of a spine segment corresponds and/or correlates with segments of the spine in the image.

Further advantages, features and examples of the present invention will be apparent from the following description of following figures.

DETAILED DESCRIPTION OF THE PREFERRED EMBODIMENTS

Figure 1:
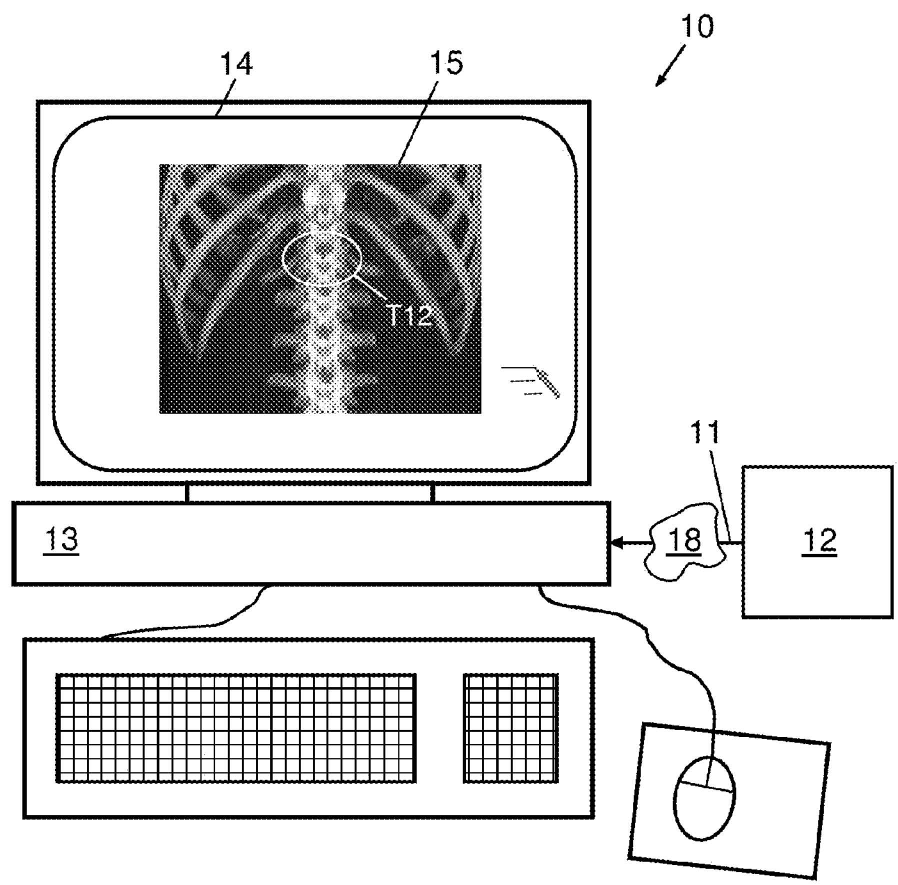
FIG. 1 shows an example of an apparatus and a system according to a preferred embodiment of the invention.

FIG. 1 shows an example of an apparatus 10 and a system according to a preferred embodiment of the invention. A medical image data set 11 comprising a plurality of images, in particular slice images, of a human or animal body is acquired by a medical imaging apparatus 12, in particular a computer tomography (CT) apparatus.

The apparatus 10 comprises a control unit 13, e.g. a workstation or a personal computer (PC), to which the image data set 11 is fed. Preferably, the image data set 11 can be transferred from the medical imaging apparatus 12 to the control unit 13 via a data network 18 to which the control unit 13 is, at least temporarily, connected. For example, the data network 18 can be a local area network (LAN) or wireless LAN (WLAN) in a hospital environment or the internet.

Preferably, the control unit 13 is configured to generate a slice view 15 and/or a volume reconstruction (not shown) of the image data set 11 on a display 14, e.g. a TFT screen of the workstation or PC, respectively.

According to a preferred embodiment of the invention, the control unit 13 is designed to identify a specific part of a spine, in particular a specific vertebra, which can preferably serve as a starting point for an algorithm for labeling one or more further parts, in particular further vertebrae and/or intervertebral discs, of the spine in the image data set 11. In the example given in FIG. 1, a vertebra T12 corresponding to the 12th thoracic vertebra was identified and accordingly labeled in the axial slice view 15 of the image data set of a spine.

In the following, the method and corresponding apparatus and system for identifying a specific vertebra, in particular the T12 vertebra, in the image data set 11 according to preferred embodiments of the invention will be elucidated in detail.

The method relates to a, preferably machine learning-based, algorithm for reliable discrimination of the $12^{th}$ thoracic vertebra T12 in lumbar-thoracic parts of CT scans by two discriminative features for separating the lumbar vertebrae from the thoracic ones. Preferably, the two discriminative features relate to the length and the angle of the attached transversal process or rib, both measured in a curved coronal projection of bones close to the spinal canal.

Preferably, the image data set 11 is a three-dimensional (3D) data set and the discriminative parameters are determined on the basis of a two-dimensional (2D) data set which is derived from the original 3D data set 11. Based on spinal canal extraction, the frontal part of the rib cage is cropped out and the remaining bones attached to the spine are projected in a frontal curved maximum intensity manner.

Post processing of this projection yields a single closed contour in 2D, further referred to as "rib contour" or "contour image". Its interior is split into vertebral segments containing 2D projections of transverse processes or ribs. For each vertebral segment, a pair of discriminative features is computed and classified with a pre-computed support vector machine (SVM). The derivation of the 2D rib contour from the 3D volume data set 11 is detailed in the following.

Detection of the spinal canal is a first logical step for any algorithm dealing with spine. Preferably, the spinal canal is detected or extracted by the method disclosed by F. Schulze, D. Major, and K. Bühler, *Fast and memory efficient feature detection using multi-resolution probabilistic boosting trees*, in *Journal of WSCG,* 19 (1):33-40, 2011, which is herewith incorporated into this patent application by reference.

Once the spinal canal is extracted, the frontal part of the rib cage is pruned, i.e. image data relating to the frontal part of the rib cage are eliminated from the image data set 11.

The remaining 3D data set is converted and/or displayed by a frontal, maximum intensity projection (MIP), wherein in the visualization plane the voxels, i.e. 3D image data, with maximum intensity that fall in the way of parallel rays traced from the viewpoint to the plane of projection are selected.

Preferably, to account for the natural spine bending, eventual scoliosis, injury deformations or similar, the MIP is adopted in a curved planar reformation (CPR) manner according to the method disclosed by A. Kanitsar, D. Fleischmann, R. Wegenkittl, P. Felkel, and M. E. Gröller, *CPR—Curved Planar Reformation, in IEEE Visualization* 2002, pages 37-44, 2002, which is herewith incorporated into this patent application by reference.

By the MIP, a 2D data set is derived from the original 3D data set. Therefore, from this point on, the rest of the algorithm according to a preferred embodiment of the invention refers to 2D data sets.

Further, the MIP projection is thresholded to obtain bone pixels. The resulting binary mask is processed by elementary image processing operations resulting in several closed connected contours. The longest one, the rib contour, contains all the lumbar vertebrae and some lower thoracic vertebrae and is a subject for further analysis.

Figure 2:
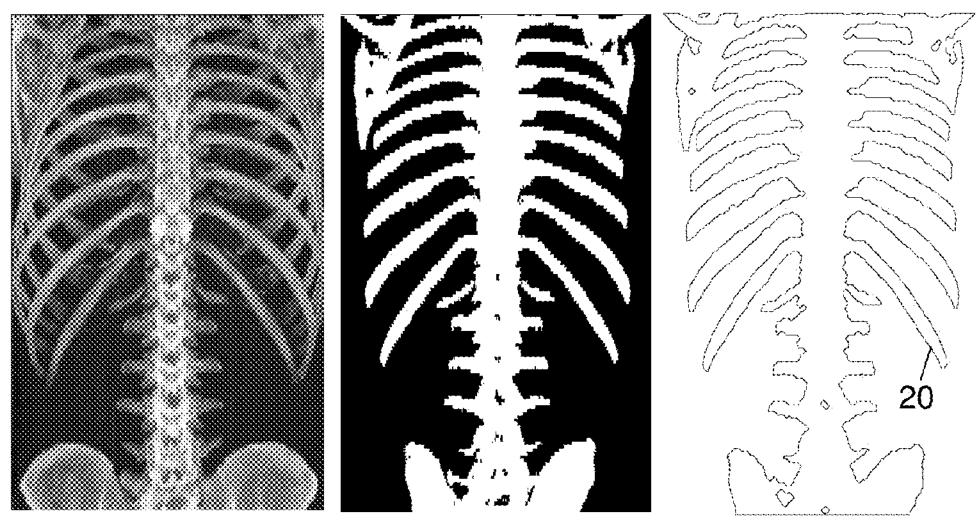
FIG. 2 shows examples of results of different processing steps of an input 3D CT scan.

The extraction of the rib contour from the 3D volume data set 11 is summarized in Algorithm 1 and illustrated by FIG. 2, which shows results of different processing steps, i.e. a maximum intensity projection of the input CT scan with a ground labeling overlay (left part), a curved planar projection of bones attached to the spine, with frontal ribs cropped out (middle part) and contours extracted from the mask, wherein the longest one is referred to as the rib contour 20 (right part).

Algorithm 1 From 3D CT to 2D rib contour

Figure 3:
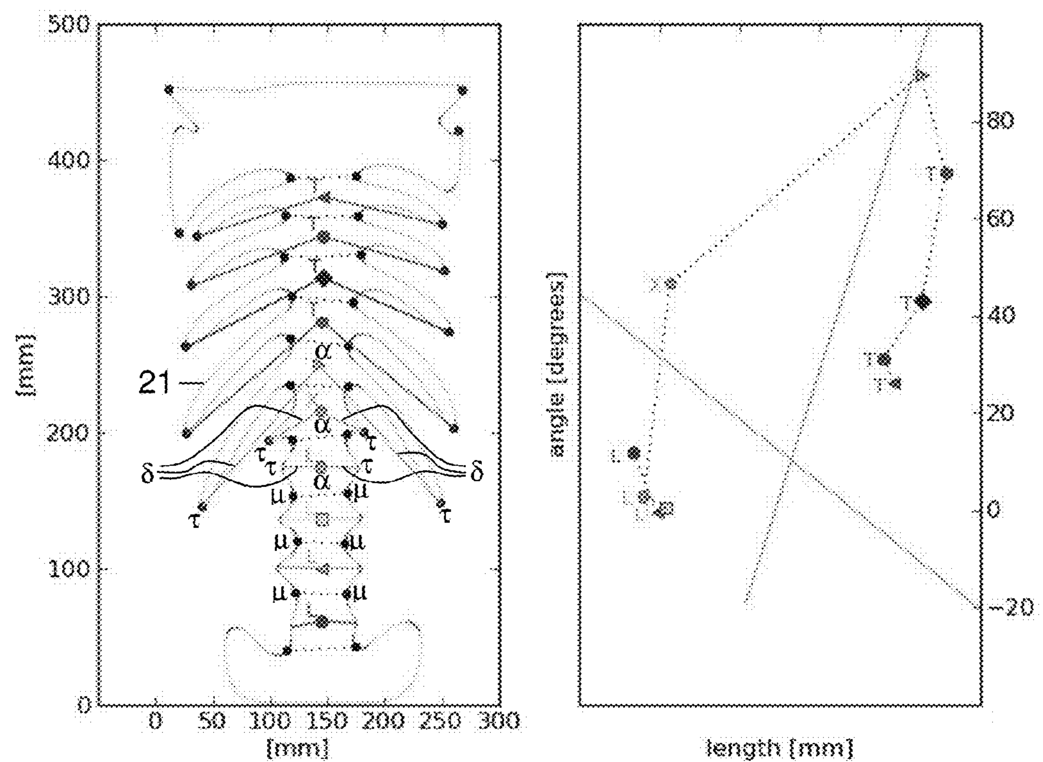
FIG. 3 shows an example of a smoothened rib contour (left) and a representation of a feature space (right), in which discriminative parameters, i.e. length and angle of connecting lines between centroids and rib/process tips of vertebrae, are plotted.

```
function GetRibContour(CT volume)              ▷ returns one contour
    Detect spinal canal
    Prune away the frontal part of rib cage
    Curved maximum intensity projection        ▷ 2D image
    Bone threshold                             ▷ fig. 2 mid
    Extract edges and connected contours       ▷ fig. 2 right
    Return the longest contour (rib contour)   ▷ fig. 3 left
end function
```

In the following, the determination of vertebra segments and respective measures, in particular discriminative parameters, will be elucidated in detail.

In order to achieve numerical stability of a subsequent analysis of the rib contour and to remove eventual outliers, the rib contour coordinates are smoothed by a Gaussian kernel. This also yields the rib contour's differentiable parameterization (x(t); y(t)), wherein x(t) and y(t) denote spatial coordinates of the contour with respect to continuous, real-valued parameter t.

To extract vertebrae segments from the smoothed rib contour, a search for local minima and maxima of signed (planar) curvatures is performed $$k = \frac{x'y'' - y'x''}{(x'^2 + y'^2)^{3/2}} \tag{1}$$

In equation (1) k denotes a signed curvature of the rib contour.

Assuming a counter-clockwise orientation of the curve, local maxima correspond to rib tips or process tips, respectively, and local minima correspond to approximate disk locations.

This is summarized in Algorithm 2 and illustrated in FIG. 3 (left), which shows a smoothed rib contour 21 with local minima μ which approximate intervertebral disc positions and yield the segmentation (dotted lines) of the spine. For sake of clarity, only six minima μ of twenty-two minima in total are annotated with reference letter "μ".

Centroids of the segments annotated with reference letter "α" are connected to the two associated rib/process tips τ. For sake of clarity, only three centroids α of ten centroids in total (see symbols annotated with "L", "X" and "T") and six local maxima τ of twenty-four maxima in total are denoted with corresponding reference letters.

The center α of each segment is connected with the two tips τ of the associated ribs/processes via a straight line δ. Two measures, which are also called "discriminative parameters" in the context of the invention, are calculated for the connecting lines δ. Preferably, the length and the angle enclosed by the left and right part the connecting lines δ are calculated in order to get a measure for distinguishing between Λ-like (+1), dash-like (0), i.e. straight, and eventual V-like (−1) connecting line δ.

Algorithm 2 Vertebra segments and features

```
function GetSegments(RibContour)                 ▷ returns list of polylines
    Smooth rib contour
    Compute curvatures, minima and maxima        ▷ fig. 3 left, a, b
    Connect corresponding minima                 ▷ fig. 3 left, dotted lines
    Vertebra centers from curvature minima       ▷ fig. 3 left, c
    Connect centers with corresponding maxima    ▷ fig. 3 left, d
    Return list of polylines
end function
```

In the following, the identification or discrimination of the T12 vertebra based on the two calculated measures will be elucidated in detail.

It was found that lumbar polylines, i.e. connecting lines δ (see left part of FIG. 3), are short and their angles tend to cluster near zero, whereas the thoracic vertebrae are long with positive angles. The shape of the T12 ribs, however, can vary between that of lumbar processes and thoracic ribs. Thus, neither length nor angle is discriminative.

In order to reliably discriminate the T12 vertebra from other vertebrae based on the length and angle of the connecting lines δ, two linear support vector machines (SVMs) are trained: the first SVM separating the lumbar segments {L1 . . . L5} from the thoracic ones {T7 . . . T12} and the second SVM separating the {T7 . . . T11} from {T12 . . . L5}.

An SVM is a so-called classifier, which corresponds to a mathematical method for separating, i.e. classifying, an amount of objects into two or more classes. SVMs are supervised learning models with associated learning algorithms that analyze data and recognize patterns used for classification. A basic SVM takes a set of input data and predicts, for each given input, which of two possible classes forms the output, making it a non-probabilistic binary linear classifier. Given a set of training examples, each marked as belonging to one of two categories, an SVM training algorithm builds a model that assigns new examples into one category or the other. An SVM model is a representation of the examples as points in space, mapped so that the examples of the separate categories are divided by a clear gap that is as wide as possible. New examples are then mapped into that same space and predicted to belong to a category based on which side of the gap they fall on. Methods of training SVMs are disclosed by V. N. Vapnik, *The nature of statistical learning theory*, Springer-Verlag, New York, Inc., New York, N.Y., USA, 1995, which is herewith incorporated into this patent application by reference.

FIG. 3 (right) shows the calculated length and angle of feature polylines, i.e. connecting lines δ, plotted in a two-dimensional feature space. The solid lines correspond to the two pre-learned support vector machines (SVM) that split the feature space into four sub-regions, i.e. lumbar region ("L"), T12 region ("X"), thoracic region ("T") and blank. The dotted line connects the segment features in the anatomical order.

Figure 4:
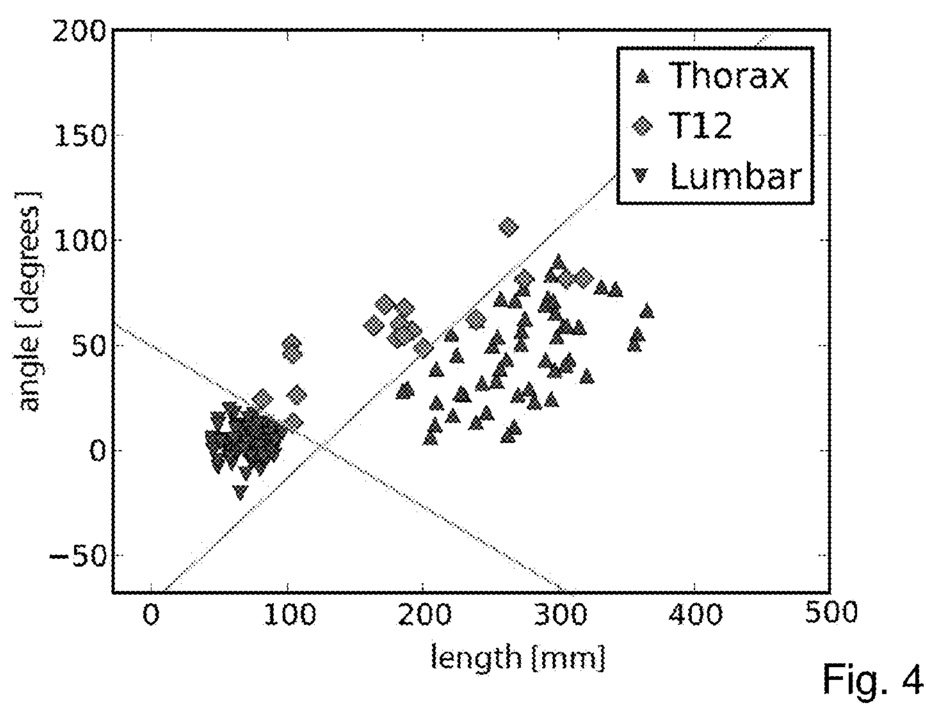
FIG. 4 shows an example of a feature space in which discriminative parameters together with two linear SVMs learned from 29 CT images are depicted.

FIG. 4 shows an example of a feature space in which discriminative parameters together with two linear SVMs learned from 29 CT images are depicted. As apparent from the example given in FIG. 4, there was no linear SVM (i.e. line) found that would clearly separate the T12 from the rest of the thoracic vertebrae, i.e., that would separate groups {T7 . . . T11} and {T12 . . . L5}, but a linear SVM was found to discriminate between the lumbar vertebrae segments {L1 . . . L5} from thoracic ones {T7 . . . T12}.

To reliably find the T12 segment in an application, all available vertebral segments are first sorted in the bottom-to-top order by the y-coordinates of the centroids α and then classified as "L", "X", or "T". In order to reliably identify the T12, there must be at least one segment classified as "L" and at least one segment classified either as "X" or "T". The first segment following the chain of "L" segments is identified as T12.

Examples of segment class strings in the bottom-to-top order with the final verdicts are given as follows:

"LLLXTTT" T12 is the $4^{th}$ segment
"LLLLTTT" T12 is the $5^{th}$ segment
"LXXT" T12 is the $2^{nd}$ segment
"TTTT" no "L" segment available, i.e., T12 is uncertain
"LLLL" only lumbar segments available, i.e., T12 is uncertain.

The invention claimed is:

1. A method for identifying a specific part of a spine in an image of a human or animal body, the method comprising the steps of:

determining one or more parts of the spine in the image;

determining one or more discriminative parameters for each of the one or more parts of the spine in the image, the one or more discriminative parameters relating to at least one anatomical property of each of the one or more parts of the spine;

classifying the one or more discriminative parameters of the one or more parts of the spine in the image; and identifying a specific part of the spine based on the classification of the one or more discriminative parameters of the one or more parts of the spine in the image; wherein the one or more parts of the spine in the image are determined on a basis of a contour image derived from the image by the following steps:

detecting a spinal canal of the spine in the image;

pruning away a frontal part of a rib cage from the image;

calculating a frontal plane maximum intensity projection of the image;

deriving a binary image from the frontal plane maximum intensity projection of the image by comparing pixel values of the maximum intensity projection with at least one bone threshold value; and deriving the contour image from the binary image.

2. The method according to claim 1, wherein the one or more discriminative parameters relate to angles between the spine and a rib contour at the one or more parts of the contour image.

3. The method according to claim 1, wherein the one or more parts of the spine in the image are determined based on the contour image by the following steps:

smoothing the contour image;

calculating local minima and local maxima in the contour image;

determining vertebra centers on a basis of the local minima and/or the local maxima;

establishing connections between the vertebra centers with corresponding local maxima; and determining the one or more discriminative parameters for each of the one or more parts of the spine in the image on a basis of the connections including lengths and/or angles of the connections.

4. An apparatus for identifying a specific part of a spine, in an image of a human or animal body, the apparatus comprising an image processor configured or programmed to:

determine one or more parts of the spine in the image;

determine one or more discriminative parameters for each of the one or more parts of the spine in the image, the one or more discriminative parameters relating to at least one anatomical property of each of the one or more parts of the spine;

classify the one or more discriminative parameters of the one or more parts of the spine in the image; and identify a specific part of the spine based on the classification of the discriminative parameters of the one or more parts of the spine in the image; wherein the one or more parts of the spine in the image are determined on a basis of a contour image derived from the image by the image processor being further configured or programmed to perform the following steps:

detect a spinal canal of the spine in the image;

prune away a frontal part of a rib cage from the image;

calculate a frontal plane maximum intensity projection of the image;

derive a binary image from the maximum intensity projection of the image by comparing pixel values of the maximum intensity projection with at least one bone threshold value; and derive the contour image from the binary image.

5. A system for identifying a specific part of a spine in an image of a human or animal body, the system comprising:

a computed tomography processor configured or programmed to acquire at least one image of at least a part of a human or animal body; and the apparatus according to claim 4.

* * * * *